United States Patent
Mehdizadeh et al.

(10) Patent No.: US 10,165,957 B2
(45) Date of Patent: *Jan. 1, 2019

(54) NEUROLOGICAL SCREENING CONNECTOR

(71) Applicant: Medtronic, Inc., Minneapolis, MN (US)

(72) Inventors: Bruce R. Mehdizadeh, Savage, MN (US); Farooq M. Francis, Somerset, WI (US); Alyse R. Stofer, Cottage Grove, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 20 days.

This patent is subject to a terminal disclaimer.

(21) Appl. No.: 15/494,044

(22) Filed: Apr. 21, 2017

(65) Prior Publication Data

US 2017/0332924 A1  Nov. 23, 2017

Related U.S. Application Data

(63) Continuation of application No. 13/084,398, filed on Apr. 11, 2011, now Pat. No. 9,655,534.

(60) Provisional application No. 61/324,052, filed on Apr. 14, 2010.

(51) Int. Cl.
| | | |
|---|---|---|
| *A61N 1/375* | (2006.01) | |
| *A61B 5/04* | (2006.01) | |
| *H01R 13/11* | (2006.01) | |
| *H01R 13/50* | (2006.01) | |
| *A61N 1/05* | (2006.01) | |
| *A61N 1/36* | (2006.01) | |
| *H01R 9/03* | (2006.01) | |

(52) U.S. Cl.
CPC ............... *A61B 5/04* (2013.01); *A61N 1/375* (2013.01); *A61N 1/3752* (2013.01); *A61N 1/3754* (2013.01); *H01R 13/111* (2013.01); *H01R 13/501* (2013.01); *A61B 2560/04* (2013.01); *A61B 2560/0406* (2013.01); *A61B 2562/227* (2013.01); *A61N 1/05* (2013.01); *A61N 1/36017* (2013.01); *H01R 9/03* (2013.01); *H01R 2201/12* (2013.01)

(58) Field of Classification Search
CPC .... A61N 1/375; A61N 1/3752; A61N 1/3754; A61B 2560/04; A61B 2560/0406; A61B 2562/225; H01R 13/111; H01R 13/501; H01R 9/03; H01R 2201/12
See application file for complete search history.

(56) References Cited

U.S. PATENT DOCUMENTS

| | | |
|---|---|---|
| 5,683,433 A | 11/1997 | Carson |
| 6,321,126 B1 | 11/2001 | Kuzma |
| 6,397,108 B1 | 5/2002 | Camps et al. |
| 7,247,798 B2 | 7/2007 | Pagoto |
| 7,347,712 B2 | 3/2008 | O'Connell |
| 7,402,083 B2 | 7/2008 | Kast et al. |

(Continued)

*Primary Examiner* — Tammie K Marlen
(74) *Attorney, Agent, or Firm* — Mueting, Raasch & Gebhardt, P.A.

(57) ABSTRACT

A medical lead screening connector includes a housing, a plurality of electrical contacts disposed within the housing, where each lead receptor channel includes at least two lead receptor contacts, and a cover hingedly attached to the housing. The cover includes a protrusion that is arranged and configured to register with one of the lead receptor channels and contacts a lead body received in the lead receptor channel when the cover is in a closed position.

20 Claims, 6 Drawing Sheets

(56) References Cited

U.S. PATENT DOCUMENTS

| | | | |
|---|---|---|---|
| 8,123,567 | B2 | 2/2012 | Kast et al. |
| 9,655,534 | B2 | 5/2017 | Mehdizadeh et al. |
| 2003/0040784 | A1 | 2/2003 | Pasternak et al. |
| 2003/0199948 | A1 | 10/2003 | Kokones et al. |
| 2005/0027326 | A1 | 2/2005 | Ries et al. |
| 2005/0177199 | A1 | 8/2005 | Hansen et al. |
| 2006/0167522 | A1 | 7/2006 | Malinowski |
| 2006/0271136 | A1 | 11/2006 | Wojciechowicz |
| 2007/0049985 | A1 | 3/2007 | Kessler et al. |
| 2008/0255630 | A1 | 10/2008 | Arisso et al. |
| 2008/0269831 | A1 | 10/2008 | Erickson |
| 2009/0018601 | A1 | 1/2009 | Deininger et al. |

NEUROLOGICAL SCREENING CONNECTOR

The present application is a continuation application of U.S. patent application Ser. No. 13/084,398, filed Apr. 11, 2011, and issued as U.S. Pat. No. 9,655,534 on May 23, 2017, which claims the benefit of U.S. Provisional Patent Application No. 61/324,052, filed Apr. 14, 2010, the disclosures of which are incorporated herein by reference, each in its entirety.

BACKGROUND

The medical device industry produces a wide variety of electronic and mechanical devices for treating patient medical conditions such as pacemakers, defibrillators, neurostimulators and therapeutic substance delivery pumps. Medical devices can be configured to be surgically implanted or connected externally to the patient receiving treatment. Clinicians use medical devices alone or in combination with therapeutic substance therapies and surgery to treat patient medical conditions. For some medical conditions, medical devices provide the best and sometimes the only therapy to restore an individual to a more healthful condition and a fuller life.

One type of medical device is an implantable neurological stimulation system that can be used to treat conditions such as pain, movement disorders, pelvic floor disorders, gastroparesis, and a wide variety of other medical conditions. The neurostimulation system typically includes a neurostimulator, a stimulation lead, and an extension. The neurostimulator can be connected to a stimulation lead that has one or more electrodes to deliver electrical stimulation to a specific location in the patient's body.

The lead and stylet combination are part of an implantable neurostimulation system. The neurostimulation lead is placed in the desired location of the body. The stylet wire and handle combination are used to give the lead stiffness during implantation and to aid in maneuvering the lead into the desired position. Once the lead is believed to be placed in the appropriate position within the body the lead, with or without the stylet, is coupled with a neurostimulation screening cable, which is connected to a neurostimulation screening device. The screening device can be programmed to send different combinations, strengths and frequencies of electrical stimulation to the patient. The screening cable provides a connection to, and electrical pathway between the stimulation lead or percutaneous extension and the neurostimulation screening device. The patient is questioned to determine if the stimulation covers the desired region of the body. Provided results are favorable the patient receives a temporary implant of the stimulation lead system. Either the stimulation lead or percutaneous extension is attached to the screening cable for a trial screening period so the patient can assess the efficacy of the system in normal life settings. The patient can be sent home with an external neurostimulator that sends electrical stimulation to the stimulation lead via the screening cable during the trial period. This trial period can range from 1 to 30 days depending on the physician and the country in which the trial occurs. This trial period is used to access the efficacy of the stimulation therapy for the patient.

BRIEF SUMMARY

The present disclosure relates to a medical lead screening connector. In particular, the present disclosure relates to a medical lead screening cable that includes a number of features that improve the performance and assist in retaining and seating a lead body in the medical lead screening connector.

In one illustrative embodiment, a medical lead screening connector includes a housing, a plurality of electrical contacts disposed within the housing, and a plurality of electrical contacts disposed within the housing, where each lead receptor channel includes at least two lead receptor contacts, and a cover hingedly attached to the housing. The cover includes a protrusion that is arranged and configured to register with the one of the lead receptor channels and contacts a lead body received in the lead receptor channel when the cover is in a closed position In another embodiment, a medical lead screening connector includes a housing, a plurality of lead receptor channels disposed within the housing, where each lead receptor channel includes at least two lead receptor contacts, and a cover hingedly attached to the housing. At least one lead receptor channels includes an elastomeric lead retainer clip arranged and configured to receive and retain a lead body disposed in the lead receptor channel.

In another embodiment, a medical lead screening connector includes a housing, a plurality of lead receptor channels disposed within the housing, where each lead receptor channel includes at least two lead receptor contacts, and a cover hingedly attached to the housing. The cover includes a plurality of lead receptor apertures along a first exterior edge of the cover. The lead receptor apertures are arranged and configured to register with the lead receptor channels when the cover is in a closed position.

These and various other features and advantages will be apparent from a reading of the following detailed description.

BRIEF DESCRIPTION OF THE DRAWINGS

The disclosure may be more completely understood in consideration of the following detailed description of various embodiments of the disclosure in connection with the accompanying drawings, in which.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying set of drawings that form a part hereof and in which are shown by way of illustration several specific embodiments. It is to be understood that other embodiments are contemplated and may be made without departing from the scope or spirit of the present disclosure. The following detailed description, therefore, is not to be taken in a limiting sense.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "lower", "upper", "beneath", "below", "above", and "on top", if used herein, are utilized for ease of description to describe spatial relationships of an element(s) to another. Such spatially related terms encompass different orientations of the device in use or operation in addition to the particular orientations depicted in the figures and described herein. For example, if a cell depicted in the figures is turned over or flipped over, portions previously described as below or beneath other elements would then be above those other elements.

As used herein, when an element, component or layer for example is described as being "on" "connected to", "coupled with" or "in contact with" another element, component or layer, it can be directly on, directly connected to, directly coupled with, in direct contact with, or intervening elements, components or layers may be on, connected, coupled or in contact with the particular element, component or layer, for example. When an element, component or layer for example is referred to as begin "directly on", "directly connected to", "directly coupled with", or "directly in contact with" another element, there are no intervening elements, components or layers for example.

The present disclosure relates to a medical lead screening connector. In particular, the present disclosure relates to a medical lead screening cable that includes a number of features that improve the performance and assist in retaining and seating a lead body in the medical lead screening connector. For example, the cover can articulate 180 degrees from an open position to a closed position. The cover can include one or more protrusions that assist in seating a lead body that is received in lead receptor channel of the medical lead screening connector when the cover is in the closed position. An elastomeric lead retainer clip can be disposed within the lead receptor channel to receive and retain a lead body that is received in lead receptor channel of the medical lead screening connector. The cover can also include one or more lead receptor apertures along an exterior edge of the cover where the lead receptor apertures are arranged and configured to register with the lead receptor channels when the cover is in a closed position The medical lead screening connector can also include redundant locking features to securely maintain the cover in the closed position. While the present disclosure is not so limited, an appreciation of various aspects of the disclosure will be gained through a discussion of the examples provided below.

The teachings presented herein are applicable to any implantable medical device system employing lead for delivering electrical signals to a tissue of a patient. For example, the system may include a neurostimulator, such as a peripheral nerve stimulator, a spinal cord stimulator, or a deep brain stimulator; a cardiac pacemaker or defibrillator; a gastric stimulator; or the like. It will be understood that the systems and devices described herein may be readily applied to systems employing leads for purposes of screening, sensing, monitoring, recording, or the like.

Figure 1:
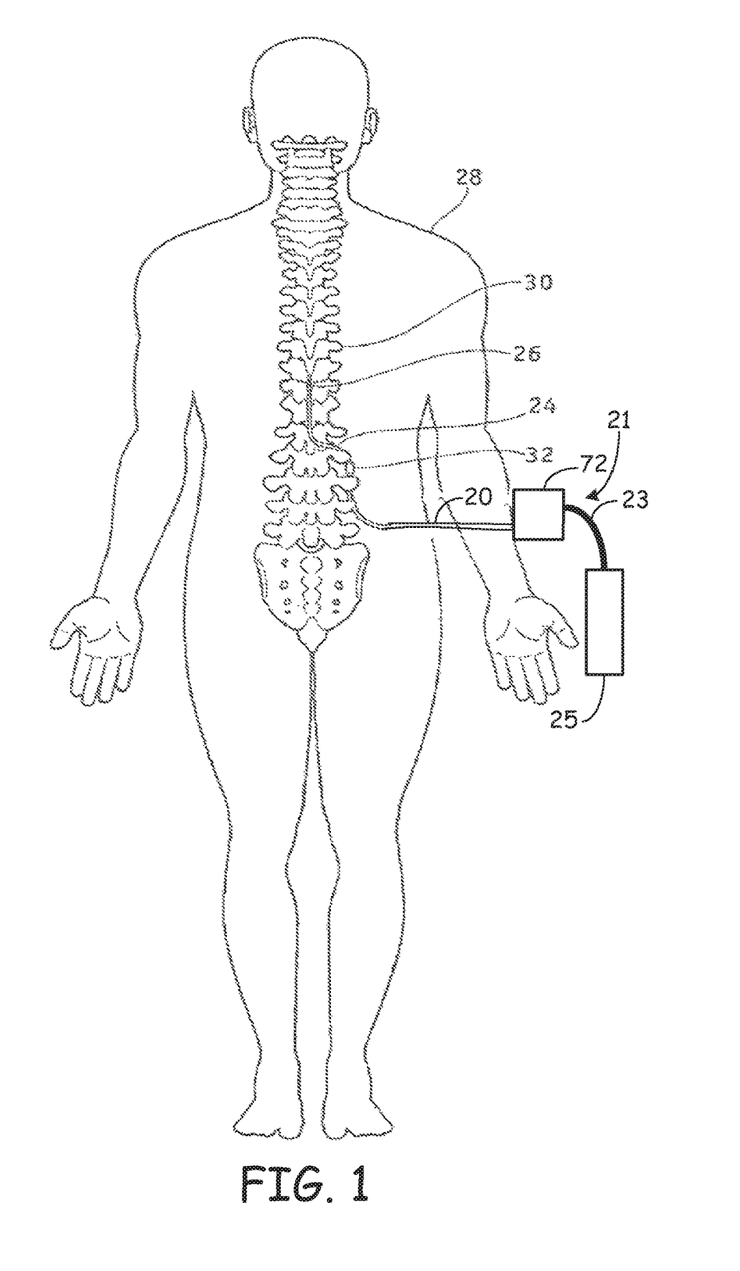
FIG. 1 is a schematic diagram of a neurological lead implanted within a human body or patient.

FIG. 1 is a schematic diagram of a neurological lead 24 implanted within a human body or patient 28. The implanted neurological lead 24 is a medical wire with special insulation. The neurological lead 24 includes one or more insulated electrical conductors with a connector on the proximal end and electrical contacts on the distal end. Some neurological leads are designed to be inserted into a patient percutaneously, and some neurological leads are designed to be surgically implanted. The neurological lead 24 may also be a paddle having a plurality of electrodes. Those skilled in the art will appreciate that any variety of neurological leads 24 may be used.

The neurological lead 24 can be implanted and positioned to stimulate a specific site in the spinal cord 30 or the nervous system. The neurological lead 24 includes one or more electrodes 26 (small electrical contacts) through which electrical stimulation is delivered from a either an external stimulator 25 or an implanted stimulator (not shown) to the targeted neural tissue. The external stimulator 25 or an implanted stimulator can be any "active medical device" or "signal generator" as described above and can be placed external to or in any location within a body cavity or tissue within the body, or on the surface of a patient's skin, as desired.

The external stimulator 25 can be used to test the efficacy of stimulation therapy for the patient before an implantable stimulator is surgically implanted. The external stimulator 25 is used in conjunction with a screening cable 21 which accepts the stimulation lead 24 or lead extension 20 and creates an electrical pathway to the external stimulator 25. The screening cable 21 includes a conductor cable 23 and a distal screening connector 72 that includes pivoting lead receptacles (described below). The conductor cable 23 electrically connects the lead receptacles within the distal screening connector 72 to the external stimulator 25.

The illustrated external stimulator 25 is coupled to a lead extension 20 via the screening cable 21. The lead extension 20 has a proximal end coupled to the screening cable 21, and a lead 24 having a proximal end coupled to a distal end 32 of the lead extension 20 and a distal end of the lead 24 coupled to one or more electrodes 26. In some embodiments, the lead 24 proximal end is coupled to the screening cable 21, without a need for a lead extension. In many embodiments, the screening cable 21 couples to one or two or more leads each having four to eight electrodes. Such a system may also include a physician programmer and a patient programmer (not shown). The external stimulator 25 can be considered to be a signal generator of the type available from Medtronic, Inc. and capable of generating multiple signals occurring either simultaneously or one signal shifting in time with respect to the other, and having independently varying amplitudes and signal widths. The external stimulator 25 can contain a power source and the electronics for sending precise, electrical signals to the patient to provide the desired treatment therapy. While the external stimulator 25, in many embodiments, provides electrical stimulation by way of signals, other forms of stimulation may be used as continuous electrical stimulation.

In many embodiments, the lead 24 is a wire having insulation thereon and includes one or more insulated electrical conductors each coupled at their proximal end to a connector and to contacts/electrodes 26 at its distal end. Some leads are designed to be inserted into a patient percutaneously, and some are designed to be surgically implanted. In some embodiments, the lead 24 may contain a paddle at its distant end for housing electrodes 26. In many embodiments, electrodes 26 may include one or more ring contacts at the distal end of lead 24.

Figure 2:
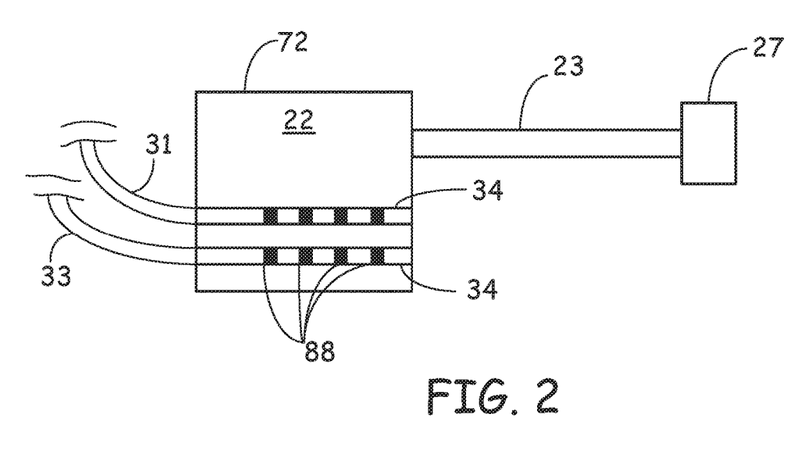
FIG. 2 is a schematic diagram of an illustrative screening cable.

FIG. 2 is a schematic diagram of an illustrative screening cable 21. The screening cable 21 includes a proximal screening connector 27 electrically coupled to lead receptacles 34 in the lead connector housing 22 of the distal screening connector 72. Conductor wires are disposed within the conductor cable 23 electrically coupled the lead receptacles 34 to the proximal screening connector 27. While two lead receptacles are illustrated, it is understood that the distal screening connector 72 can include any number of lead receptacles, as desired. In some embodiments, the distal screening connector 72 can be directly electrically coupled to a lead screening device or programming device (e.g., external stimulation device).

A first implantable medical lead 31 and second implantable medical lead 33 are received in the lead receptacles 34. The lead receptors 34 are configured for receiving the first implantable medical lead 31 and a second implantable medical lead 33. Electrical contacts on the lead 31, 33 mates with electrical contacts 88 within the distal screening connector 72.

The first implantable medical lead 31 and a second implantable medical lead 33 can be a wide variety of medical leads, such as, a neurological lead. In some embodiments the medical lead can be a four-conductor neurological lead, a four-conductor extension, a four-conductor neurological lead with stylet handle, a four conductor percutaneous extension with stylet handle, an eight-conductor neurological lead, an eight-conductor extension, an eight-conductor neurological lead with stylet handle, and the like.

Figure 3:
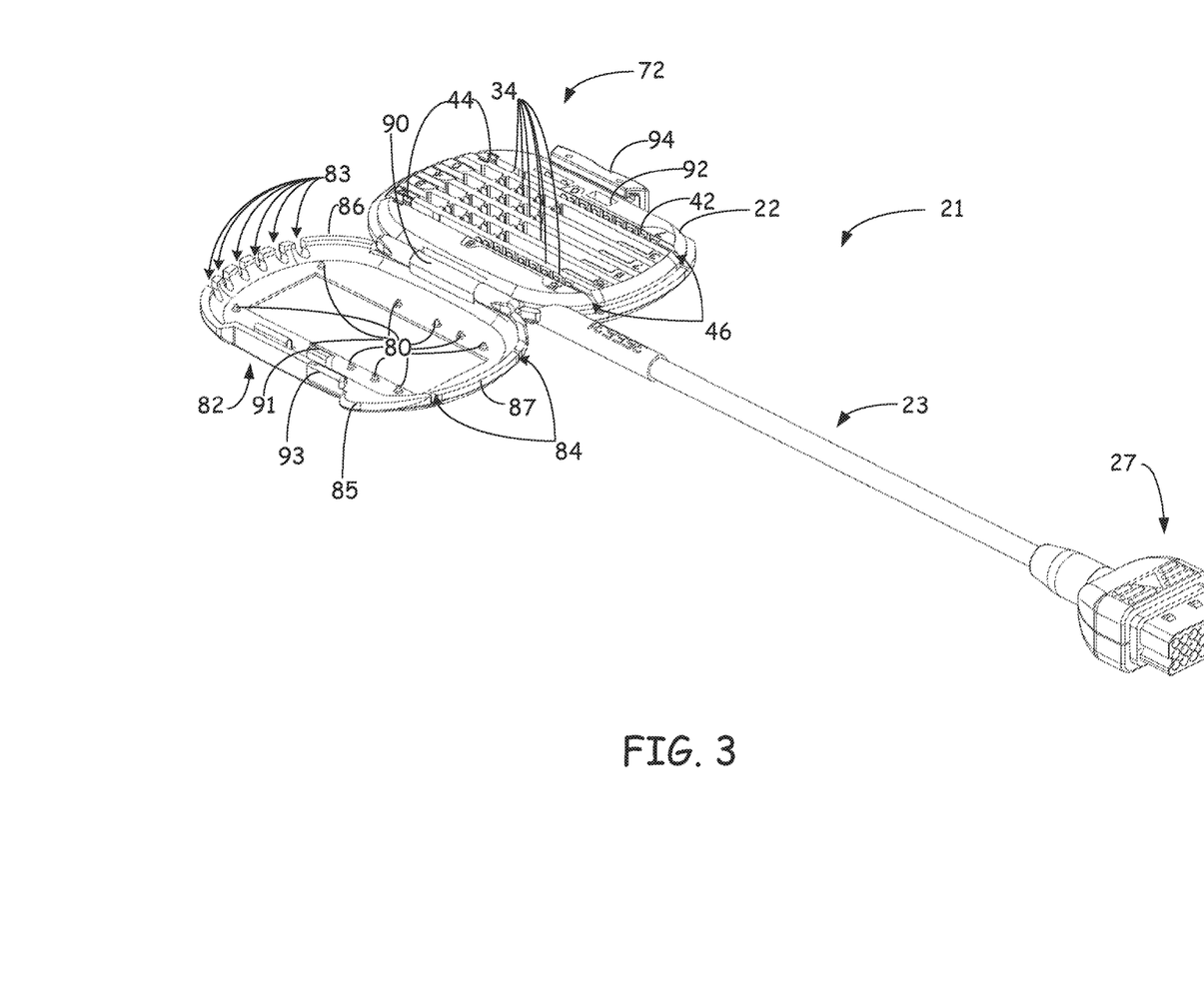
FIG. 3 is a schematic diagram perspective view of an illustrative screening cable with the cover of the lead screening connector in the open position.
Figure 4:
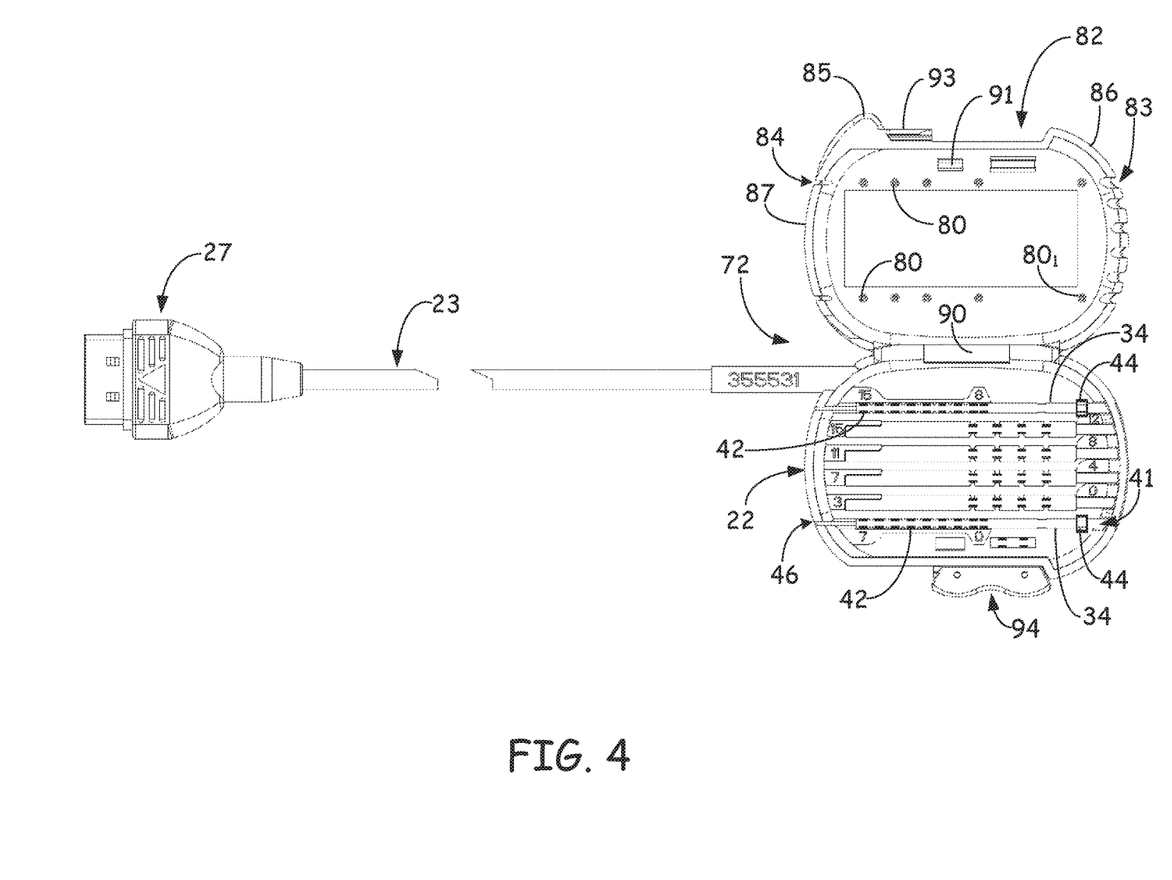
FIG. 4 is a schematic diagram front view of an illustrative screening cable housing with the cover of the lead screening connector in the open position.
Figure 5:
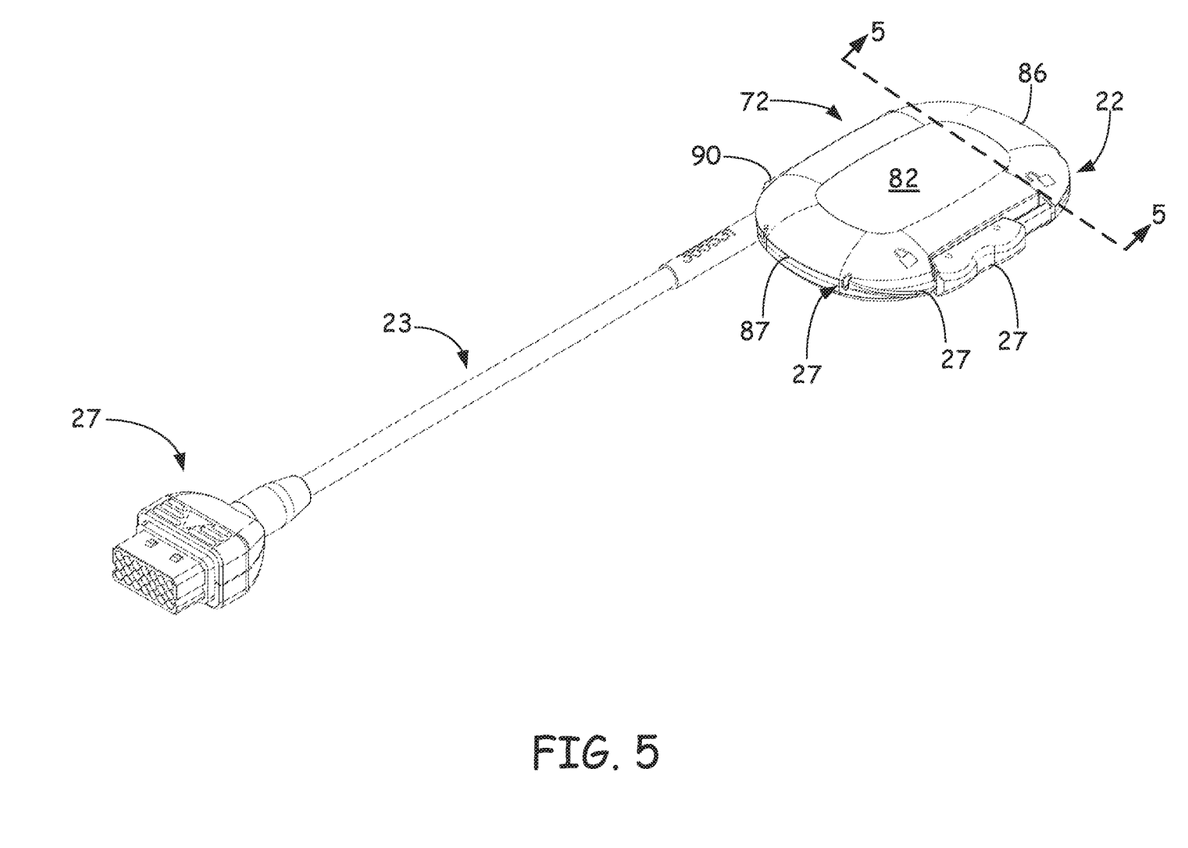
FIG. 5 is a schematic diagram perspective view of an illustrative screening cable with the cover of the lead screening connector in the closed position.
Figure 6:
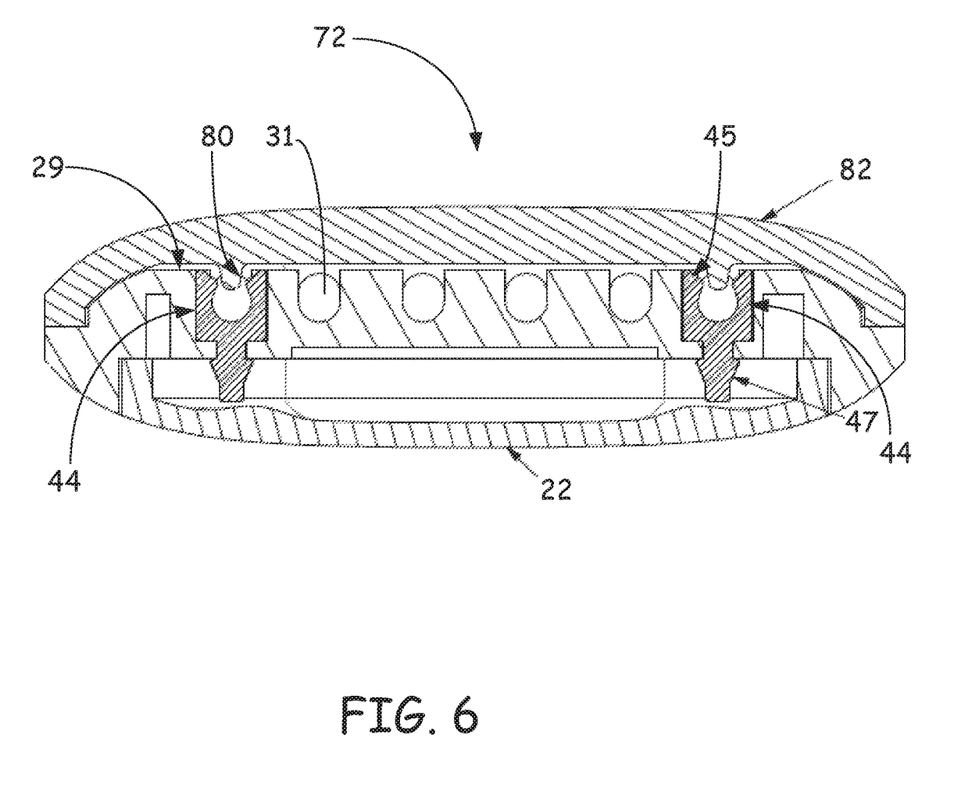
FIG. 6 is a schematic diagram cross-sectional view of the illustrative screening cable taken along lines 6-6 of FIG. 5.

FIG. 3 is a schematic diagram perspective view of an illustrative screening cable with the cover of the lead screening connector in the open position. FIG. 4 is a schematic diagram front view of an illustrative screening cable housing with the cover of the lead screening connector in the open position. FIG. 5 is a schematic diagram perspective view of an illustrative screening cable with the cover of the lead screening connector in the closed position. FIG. 6 is a schematic diagram cross-sectional view of the illustrative screening cable taken along lines 6-6 of FIG. 5.

The screening cable 21 includes a proximal screening connector 27 electrically coupled to lead receptacles 34 in the lead connector housing 22 of the distal screening connector 72. Conductor wires are disposed within the conductor cable 23 electrically coupled the lead receptacle 34 receptor contacts 42 to the proximal screening connector 27. While two eight contact lead receptacles and four contact lead receptacles are illustrated, it is understood that the distal screening connector 72 can include any number of lead receptacles, as desired. In some embodiments, the distal screening connector 72 can be directly electrically coupled to a lead screening device or programming device (e.g., external stimulation device) via the proximal screening connector 27.

The medical lead screening connector 72 includes a housing 22, a plurality of lead receptor channels 34 are disposed within the housing 22 and a cover 82 is hingedly attached to the housing 22. Each lead receptor channel 34 includes at least two lead receptor contacts 42. The lead receptor contacts 42 are configured to mate with the lead contacts when a lead is received in the lead receptor channel 34. The cover 82 includes a protrusion 80 that is arranged and configured to register with one of the lead receptor channels 34 and contacts a lead body received in the lead receptor channel 34 when the cover 82 is in a closed position. As illustrated in FIG. 3 and FIG. 5, the cover 82 can articulate at least 180 degrees between an open position (FIG. 3) and a closed position (FIG. 5).

In another embodiment, a medical lead screening connector 72 includes a housing 22, a plurality of lead receptor channels 34 disposed within the housing 22, where each lead receptor channel 34 includes at least two lead receptor contacts 42, and a cover 82 is hingedly attached to the housing 22. At least one lead receptor channel 34 includes an elastomeric lead retainer clip 44 arranged and configured to receive and retain a lead body disposed in the lead receptor channel 34.

In another embodiment, a medical lead screening connector 72 includes a housing 22, a plurality of lead receptor channels 34 disposed within the housing 22, where each lead receptor channel 34 includes at least two lead receptor contacts 42, and a cover 82 is hingedly attached to the housing 22. The cover 82 includes a plurality of lead receptor apertures 83 along a first exterior edge 86 of the cover 82. The lead receptor apertures 83 are arranged and configured to register with the lead receptor channels 34 when the cover 82 is in a closed position.

The housing 22 can include a cover 82 hingedly attached to the housing 22 via a hinge 90. The hinge 90 can include a housing hinge portion and a cover hinge portion. The cover 82 has a cover open position for permitting access to the lead receptor channels 34 and a cover closed position for enclosing the lead receptor channels 34 and securing a lead received in the lead receptor channels 34 in the closed position. The cover 82 can include a closing latch element 91 that assists in securing the cover 82 to a closing latch mating element 92 in the housing 22. In many embodiments, the cover 82 includes a slide lock rail 93 that assists in securing the cover 82 to a slide lock element 94 on the housing 22. Thus when the cover 82 is positioned in the closed position, closing latch element 91 engages the closing latch element 92 and the slide lock rail 93 engages the slide lock element 94. In many embodiments the cover 82 is constructed from polymer materials and materials that are transparent to visible light.

The protrusion 80 can be formed of an electrically insulating material. In many embodiments, the protrusion 80 is formed of the same polymeric material forming the cover 82, which can be transparent to visible light. The protrusion 80 can be a discrete "bump" or element having an aspect ratio 2:1 or 1:2 or substantially having a circular or oval cross-sectional area that is parallel to the major surface of the cover 82. The cover 82 can include a plurality of protrusions 80 can as illustrated. A plurality of protrusions 80 can be disposed along and in registration with a particular lead receptor channel 34. The protrusions 80 are arranged and configured to register with the one of the lead receptor channels 34 and contact a lead body received in the lead receptor channel 34 when the cover 82 is in a closed position. In some embodiments, as illustrated in FIG. 3, the cover 82 includes a first plurality of protrusions 80 that are arranged and configured to register with a first lead receptor channel 34 and contact a first lead body received in the first lead receptor channel 34 when the cover 82 is in a closed position, and the cover 82 includes a second plurality of protrusions 80 that are arranged and configured to register with a second lead receptor channel 34 and contact a second lead body received in the second lead receptor channel 34 when the cover 82 is in a closed position.

An elastomeric lead retainer clip 44 can be disposed in the lead receptor channels 34. The elastomeric lead retainer clip 44 is arranged and configured to help receive and retain a lead body disposed in the lead receptor channel 34. The elastomeric lead retainer clip 44 can be formed of an electrically insulation material. In many embodiments, the elastomeric lead retainer clip 44 includes sloping interior side walls 45 to receive the lead body (see FIG. 6). The sloping interior side walls 45 of the elastomeric lead retainer clip 44 allows a lead body to easily enter the elastomeric lead retainer clip 44 without collapsing the sloping interior side walls 45 of the elastomeric lead retainer clip 44. The elastomeric lead retainer clip 44 is disposed flush or sub-flush with a top surface 29 of the housing 22 adjacent to the elastomeric lead retainer clip 44. In some embodiments, the protrusion 80 is arranged and configured to register with the elastomeric lead retainer clip 44 and contacts a lead body received in the elastomeric lead retainer clip 44 when the cover 82 is in a closed position. The elastomeric lead retainer clip 44 can be anchored to the housing 22 with a post 47 and the elastomeric lead retainer clip 44 and post 47 can be an integral element.

The cover 82 can include a plurality of lead receptor apertures 83 along a first exterior edge 86 of the cover 82. The lead receptor apertures 83 are arranged and configured to register with the lead receptor channel or lead receptor channel apertures 41 when the cover 82 is in a closed position. In some embodiments, the cover 82 further includes a stylet receptor aperture 84 along a second exterior edge 87 of the cover 82. The second exterior edge 87 opposes the first exterior edge 86. The stylet receptor aperture 84 is arranged and configured to register with lead receptor channel stylet apertures 46 when the cover 82 is in a closed position. In some embodiments, the cover 82 includes a plurality of lead receptor apertures 83 along a first exterior edge 86 of the cover 82, and at least one lead receptor aperture 83 is aligned with the plurality of protrusions 80.

Thus, embodiments of the NEUROLOGICAL SCREENING CONNECTOR are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation, and the present invention is limited only by the claims that follow.

What is claimed is:

1. A medical lead screening connector comprising:
   a housing having a top surface;
   lead receptor channels disposed within the housing and configured to receive a lead body flush or sub-flush with the top surface; and
   a cover comprising transparent material attached to the housing to cover the top surface in a closed position, wherein the cover further comprises:
   protrusions arranged to register with the at least one of the lead receptor channels and each configured to contact the lead body received in the respective lead receptor channel in the closed position; and
   lead receptor apertures configured to allow the lead body to pass through the cover along a first exterior edge of the cover and registered with the lead receptor channels in the closed position.

2. The medical lead screening connector according to claim 1, wherein the protrusions comprise transparent material.

3. The medical lead screening connector according to claim 1, wherein one or more of the protrusions defines a circular cross-sectional area parallel to a major surface of the cover.

4. The medical lead screening connector according to claim 1, further comprising an electrically insulating elastomeric lead retainer clip disposed in one of the lead receptor channels and the electrically insulating elastomeric lead retainer clip having side walls defining a void to receive and retain the lead body.

5. The medical lead screening connector according to claim 4, wherein one of the protrusions registers with the elastomeric lead retainer clip void and protrudes into the void in the closed position.

6. A medical lead screening connector according to claim 1, wherein the protrusions are arranged to register with at least two lead receptor channels in the closed position and aligned to at least two of the lead receptor apertures.

7. The medical lead screening connector according to claim 1, wherein the cover comprises a first set of protrusions that are arranged and configured to register with a first lead receptor channel and contact a first lead body received in the first lead receptor channel in the closed position, and the cover comprises a second set of protrusions that are arranged and configured to register with a second lead receptor channel and contact a second lead body received in the second lead receptor channel in a closed position.

8. The medical lead screening connector according to claim 1, wherein the cover is hingedly attached to the housing.

9. The medical lead screening connector according to claim 8, wherein the cover can articulate at least 180 degrees between an open and the closed position.

10. The medical lead screening connector according to claim 1, wherein the cover further includes a stylet receptor aperture along a second exterior edge of the cover through which a stylet can extend, the second exterior edge opposing the first exterior edge, the stylet receptor aperture registers with the lead receptor channel when the cover is in a closed position.

11. A medical lead screening connector according to claim 1, wherein the cover includes a slide lock rail and the housing includes a slide lock element configured to engage the slide lock rail in the closed position.

12. A medical lead screening connector according to claim 11, wherein the cover further includes a closing latch element and the housing includes a closing latch mating element configured to engage the closing latch in the closed position.

13. A medical lead screening connector comprising:
    a housing having a top surface;
    lead receptor channels disposed within the housing and configured to receive a lead body flush or sub-flush with the top surface; and
    a cover comprising transparent material attached to the housing to cover the top surface in a closed position, wherein the cover comprises:
    discrete protrusions arranged to register with at least one of the lead receptor channels and each configured to contact the lead body received in the respective lead receptor channel in the closed position; and lead receptor apertures configured to allow the lead body to pass through the cover along a first exterior edge of the cover and registered with the lead receptor channels in the closed position.

14. The medical lead screening connector according to claim 13, further comprising an elastomeric lead retainer clip disposed in one of the lead receptor channels and the elastomeric lead retainer clip having side walls defining a void to receive and retain the lead body.

15. A medical lead screening connector according to claim 14, wherein the elastomeric lead retainer clip is formed of an electrically insulating material.

16. A medical lead screening connector according to claim 14, wherein the elastomeric lead retainer clip comprises sloping interior side walls to receive the lead body.

17. A medical lead screening connector according to claim 14, wherein the elastomeric lead retainer clip is disposed flush or sub-flush with a top surface of the housing adjacent to the elastomeric lead retainer clip.

18. A medical lead screening connector comprising:

a housing having a top surface;

lead receptor channels disposed within the housing and configured to receive a lead body flush or sub-flush with the top surface; and a cover comprising transparent material attached to the housing to cover the top surface, wherein the cover comprises:

discrete electrically insulating protrusions each configured to protrude into one of the lead receptor channels to contact the lead body received in the lead receptor channel in the closed position; and lead receptor apertures along a first exterior edge of the cover configured to allow the lead body to pass through the cover and registered with the lead receptor channels in the closed position.

19. The medical lead screening connector according to claim 18, wherein the cover further includes a stylet receptor aperture along a second exterior edge of the cover through which a stylet can extend, the second exterior edge opposing the first exterior edge, the stylet receptor aperture registers with the lead receptor channel when the cover is in a closed position.

20. The medical lead screening connector according to claim 18, wherein the cover includes a slide lock rail and the housing includes a slide lock element configured to engage the slide lock rail in the closed position.

* * * * *